US008288315B2

(12) United States Patent  (10) Patent No.: US 8,288,315 B2
Voeste et al.  (45) Date of Patent: Oct. 16, 2012

(54) FUNGICIDE MIXTURES

(75) Inventors: Dirk Voeste, Limburgerhof (DE); Carola Reinecke, Limburgehof (DE); Frank Werner, Neustadt (DE); Egon Haden, Kleinniedesheim (DE)

(73) Assignee: BASF SE, Ludwigshafen (DE)

( * ) Notice: Subject to any disclaimer, the term of this patent is extended or adjusted under 35 U.S.C. 154(b) by 283 days.

(21) Appl. No.: 12/595,059

(22) PCT Filed: Apr. 7, 2008

(86) PCT No.: PCT/EP2008/054132
§ 371 (c)(1),
(2), (4) Date: Oct. 8, 2009

(87) PCT Pub. No.: WO2008/132021
PCT Pub. Date: Nov. 6, 2008

(65) Prior Publication Data
US 2010/0062938 A1  Mar. 11, 2010

(30) Foreign Application Priority Data
Apr. 25, 2007 (EP) .................................. 07106953

(51) Int. Cl.
*A01N 43/653* (2006.01)
*A01N 43/50* (2006.01)
*A01P 3/00* (2006.01)

(52) U.S. Cl. .................. 504/100; 514/383; 514/399

(58) Field of Classification Search .................. 514/383, 514/399; 504/100
See application file for complete search history.

(56) References Cited

U.S. PATENT DOCUMENTS

| | | | |
|---|---|---|---|
| 3,991,071 A | 11/1976 | Brookes et al. | |
| 4,938,792 A | 7/1990 | Kumazawa et al. | |
| 5,013,659 A | 5/1991 | Bedbrook et al. | |
| 5,476,868 A | 12/1995 | Wingert et al. | |
| 5,877,194 A | 3/1999 | Colliot et al. | |
| 5,972,971 A | 10/1999 | Heuer et al. | |
| 2002/0137759 A1 | 9/2002 | Schneidersmann et al. | |
| 2003/0130119 A1 | 7/2003 | Watrin | |
| 2005/0119229 A1 | 6/2005 | Ammermann et al. | |
| 2007/0093543 A1 | 4/2007 | Begliomini et al. | |
| 2008/0039481 A1* | 2/2008 | Kemper et al. | 514/266.23 |
| 2008/0153824 A1 | 6/2008 | Speakman et al. | |
| 2008/0306119 A1 | 12/2008 | Steiner et al. | |
| 2011/0105576 A1* | 5/2011 | Zeun et al. | 514/383 |

FOREIGN PATENT DOCUMENTS

| | | |
|---|---|---|
| AU | 735903 | 10/1999 |
| CN | 1030232 | 1/1989 |
| DE | 195 48 873 | 7/1997 |
| EP | 0 142 924 | 5/1985 |
| EP | 0 193 259 | 9/1986 |
| EP | 0 242 236 | 10/1987 |
| EP | 0 242 246 | 10/1987 |
| EP | 0 257 993 | 3/1988 |
| EP | 0 267 778 | 5/1988 |
| EP | 0 645 091 | 3/1995 |
| EP | 0 951 831 | 10/1999 |
| WO | WO 91/13972 | 9/1991 |
| WO | WO 91/19806 | 12/1991 |
| WO | WO 92/00377 | 1/1992 |
| WO | WO 92/11376 | 7/1992 |
| WO | WO 92/14827 | 9/1992 |
| WO | WO 95/00303 | 1/1995 |
| WO | WO 95/12314 | 5/1995 |
| WO | WO 99/48366 | 9/1999 |
| WO | WO 00/28825 | 5/2000 |
| WO | WO 02/102148 | 12/2002 |
| WO | WO 03/075653 | 9/2003 |
| WO | WO 2005/051081 | 6/2005 |
| WO | WO 2005/058040 | 6/2005 |
| WO | WO 2005/122772 | * 12/2005 |
| WO | WO 2006/037634 | 4/2006 |
| WO | WO 2006/066810 | 6/2006 |
| WO | WO 2008/095913 | 8/2008 |

OTHER PUBLICATIONS

HCAPLUS abstract 1980:599090 (1980).*
International Search Report completed Feb. 13, 2009, in International Application No. PCT/EP2008/054132, filed Apr. 7, 2008.
English language translation of the International Preliminary Report on Patentability from corresponding International Application No. PCT/EP2008/054132, filed Apr. 7, 2008.
Research Disclosure 207002, Jul. 2006 (Published digitally May 31, 2006).
HCAPLUS Abstract 1993:228183 (1993).
Office Action dated Mar. 21, 2012 from co-pending U.S. Appl. No. 12/525,321.

* cited by examiner

*Primary Examiner* — John Pak
(74) *Attorney, Agent, or Firm* — Brinks Hofer Gilson & Lione

(57) ABSTRACT

Fungicidal mixtures comprising, as active components:
1) metconazole of the formula I

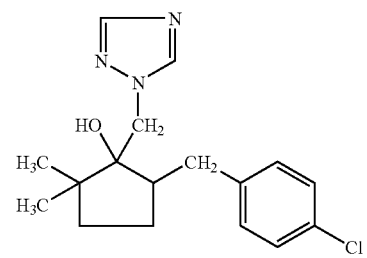

and
2) prochloraz of the formula II,

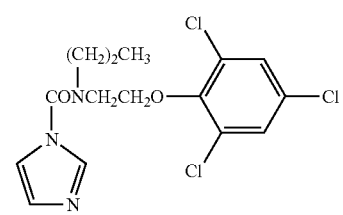

in a synergistically effective amount, and also compositions comprising these mixtures.

13 Claims, No Drawings

FUNGICIDE MIXTURES

This application is a National Stage application of International Application No. PCT/EP2008/054132 filed Apr. 7, 2008, the entire contents of which is hereby incorporated herein by reference. This application also claims the benefit under 35 U.S.C. §119 of European Patent Application No. 07106953.8 filed Apr. 25, 2007, the entire contents of which is hereby incorporated herein by reference.

DESCRIPTION

The present invention relates to fungicidal mixtures comprising, as active components,
1) metconazole of the formula I

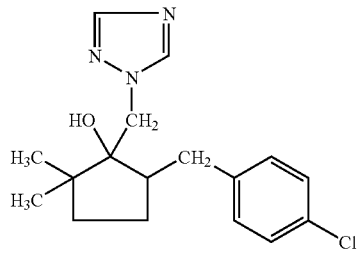

and
2) prochloraz of the formula II,

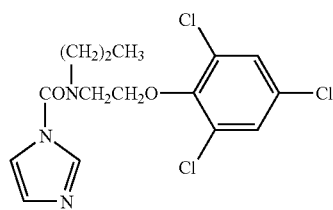

in a synergistically effective amount.

Moreover, the invention relates to a method for controlling harmful fungi using mixtures of the compound I and the compound II, and to the use of the compound I and the compound II for preparing such mixtures, and also to compositions comprising these mixtures.

Metconazole, referred to above as component 1, is (1RS, 5RS;1RS,5SR)-5-(4-chlorobenzyl)-2,2-dimethyl-1-(1H-1,2, 4-triazol-1-ylmethyl)cyclopentanol, whose preparation and whose action against harmful fungi are known from the literature (EP-A 267 778).

The active compound prochloraz, referred to above as component 2, is N-propyl-N-[2-(2,4,6-trichlorophenoxy) ethyl]imidazole-1-carboxamide, whose preparation and whose action against harmful fungi are likewise known (U.S. Pat. No. 3,991,071).

EP-A 0 951 831 discloses a concentrated liquid fungicidal composition consisting of a carrier, an azole, which also includes metconazole, a further fungicidally active component as a finely divided suspension, a solubilizer and a dispersant. The further fungicidally active components mentioned are a long list of fungicides which also comprises prochloraz. The only mixtures described are metconazole with kresoxim-methyl and chlorothalonil. The object of the invention which forms the basis of this application was that of concentrated stable coformulations.

With a view to reducing the application rates and broadening the activity spectrum of the known compounds, it was an object of the present invention to provide mixtures which, at a reduced total amount of active compounds applied, show improved activity against harmful fungi, in particular for certain indications.

Accordingly we have found the mixtures defined at the outset. Moreover, it has been found that simultaneous, that is joint or separate, application of compound I and compound II, or compound I and compound II applied in succession, allows better control of harmful fungi than with the individual compounds (synergistic mixtures). Simultaneous, that is joint or separate, application of compound I and compound II increases the fungicidal activity in a superadditive manner.

The mixtures of compound I and compound II, or the simultaneous, that is joint or separate, use of compound I and compound II are distinguished by an invigorating and yield-increasing effect on plants, in particular leguminous plants, and excellent efficacy against a broad spectrum of phytopathogenic fungi, in particular from the classes of the Ascomycetes, Deuteromycetes, Basidiomycetes and Peronosporomycetes (syn. Oomycetes). Some of them are systemically effective and can be employed in crop protection as foliar fungicides, as fungicides for seed dressing and as soil fungicides.

They are of particular importance for the control of a large number of fungi on various crop plants such as bananas, cotton, vegetable species (for example cucumbers, beans and cucurbits), barley, grass, oats, coffee, potatoes, corn, fruit plants, rice, rye, soybeans, tomatoes, grapevines, wheat, ornamental plants, sugar cane and a large number of seeds.

They are advantageously suitable for controlling the following plant diseases:
*Alternaria* species on vegetable species, oilseed rape, sugar beet and fruit and rice, such as, for example,
*A. solani* or *A. alternata* on potatoes and tomatoes,
*Aphanomyces* species on sugar beet and vegetable species,
*Ascochyta* species on cereals and vegetable species,
*Bipolaris* and *Drechslera* species on corn, cereals, rice and lawn, such as, for example, *D. maydis* on corn,
*Blumeria graminis* (powdery mildew) on cereals,
*Botrytis cinerea* (gray mold) on strawberries, vegetable species, flowers and grape-vines,
*Bremia lactucae* on lettuce,
*Cercospora* species on corn, soybeans, rice and sugar beet,
*Cochlibolus* species on corn, cereals, rice, such as, for example, *Cochliobolus sativus* on cereals, *Cochliobolus miyabeanus* on rice,
*Colletotricum* species on soybeans and cotton,
*Drechslera* species, *Pyrenophora* species on corn, cereals, rice and lawn, such as, for example, *D. teres* on barley or *D. tritici-repentis* on wheat,
*Esca* on grapevines, caused by *Phaeoacremonium chlamydosporium*, *Ph. Aleophilum*, and *Formitipora punctata* (syn. *Phellinus punctatus*),
*Elsinoe ampelina* on grapevines,
*Exserohilum* species on corn,
*Elysiphe cichoracearum* and *Sphaerotheca fuliginea* on cucumber species,
*Fusarium* and *Verticillium* species on various plants, such as, for example, *F. graminearum* or *F. culmorum* on cereals or *F. oxysporum* on a large number of plants, such as, for example, tomatoes,

*Gaeumanomyces graminis* on cereals,
*Gibberella* species on cereals and rice (for example *Gibberella fujikuroi* on rice),
*Glomerella cingulata* on grapevines and other plants,
Grainstaining complex on rice,
*Guignardia budwelli* on grapevines,
*Helminthosporium* species on corn and rice,
*Isariopsis clavispora* on grapevines,
*Michrodochium nivale* on cereals,
*Mycosphaerella* species on cereals, bananas and peanuts, such as, for example, *M. graminicola* on wheat or *M. fijiensis* on bananas,
*Peronospora* species on cabbage and bulbous plants, such as, for example, *P. brassicae* on cabbage or *P. destructor* on onion,
*Phakopsara pachyrhizi* and *Phakopsara meibomiae* on soybeans,
*Phomopsis* species on soybeans and sunflowers, *P. viticola* on grapevines,
*Phytophthora infestans* on potatoes and tomatoes, *Phytophthora* species on various plants, such as, for example, *P. capsici* on bell-peppers,
*Plasmopara viticola* on grapevines,
*Podosphaera leucotricha* on apple,
*Pseudocercosporella herpotrichoides* on cereals,
*Pseudoperonospora* on various plants, such as, for example, *P. cubensis* on cucumber or *P. humili* on hops,
*Pseudopezicula tracheiphillai* on grapevines,
*Puccinia* species on various plants, such as, for example, *P. triticina, P. striformins, P. hordei* or *P. graminis* on cereals, or *P. asparagi* on asparagus,
*Pyricularia oryzae, Corticium sasakii, Sarocladium oryzae, S. attenuatum, Entyloma oryzae* on rice,
*Pyricularia grisea* on lawn and cereals,
*Pythium* spp. on lawn, rice, corn, cotton, oilseed rape, sunflowers, sugar beet, vegetable species and other plants, such as, for example, *P. ultiumum* on various plants, *P. aphanidermatum* on lawn,
*Rhizoctonia* species on cotton, rice, potatoes, lawn, corn, oilseed rape, potatoes, sugar beet, vegetable species and on various plants, such as, for example, R. solanion beets and various plants,
*Rhynchosporium secalis* on barley, rye and triticale,
*Sclerotinia* species on oilseed rape and sunflowers,
*Septoria tritici* and *Stagonospora nodorum* on wheat,
*Erysiphe* (syn. Uncinula) necator on grapevines,
*Setospaeria* species on corn and lawn,
*Sphacelotheca reilinia* on corn,
*Thievaliopsis* species on soybeans and cotton,
*Tilletia* species on cereals,
*Ustilago* species on cereals, corn and sugar cane, such as, for example, *U. maydis* on corn,
*Venturia* species (scab) on apples and pears, such as, for example, *V. inaequalis* on apple.

The mixtures of the compounds I and II are furthermore suitable for controlling harmful fungi in the protection of materials (for example wood, paper, paint dispersions, fibers or fabrics) and in the protection of stored products. In the protection of wood, particular attention is paid to the following harmful fungi: Ascomycetes, such as *Ophiostoma* spp., *Ceratocystis* spp., *Aureobasidium pullulans, Sclerophoma* spp., *Chaetomium* spp., *Humicola* spp., *Petriella* spp., *Trichurus* spp.; Basidiomycetes, such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes, such as *Aspergillus* spp., *Cladosporium* spp., *Penicillium* spp., *Trichoderma* spp., *Alternaria* spp., *Paecilomyces* spp. and Zygomycetes, such as *Mucor* spp., additionally in the protection of materials the following yeasts: *Candida* spp. and *Saccharomyces cerevisae.*

The mixtures of the compounds I and II may additionally be used in crop plants which tolerate the action of herbicides, fungicides or insecticides as a result of breeding including genetical engineering methods.

The mixtures according to the invention may be used, for example, for transgenic plants which are resistant to herbicides of the group of the sulfonylureas, imidazolinones, glufosinate-ammonium or glyphosate-isopropylammonium and analogous active compounds (EP-A 0 242 236, EP-A 0 242 246, WO 92/00377, EP-A 0 257 993, U.S. Pat. No. 5,013,659). Or they can be used in transgenic crop plants, for example wool having the ability to produce *Bacillus thuringiensis* toxins (Bt toxins), which imparts to the plant resistance to certain pests (EP-A 0 142 924, EP-A 0 193 259).

Furthermore, the mixtures according to the invention may also be used for the treatment of plants having modified properties. They can be produced, for example, by conventional breeding methods by producing mutants. Also known is the recombinant modification of crop plants for modifying the starch synthesized in the plants (WO 92/11376, WO 92/14827, WO 91/19806). It is furthermore possible to treat crop plants producing a modified fatty acid (WO 91/13972) with the mixtures according to the invention.

The compounds I and II can be applied simultaneously, that is jointly or separately, or in succession, the sequence, in the case of separate application, generally not having any effect on the result of the control measures.

In certain circumstances it may be advantageous to add one or more further active compounds to the active compounds I and II.

The following list of fungicides, with which the compounds according to the invention can be used in conjunction, is intended to illustrate the possible combinations but does not limit them:

azoles
  triazoles: bitertanol, bromuconazole, cyproconazole, difenoconazole, diniconazole, enilconazole, epoxiconazole, fenbuconazole, flusilazole, fluquinconazole, flutriafol, hexaconazole, imibenconazole, ipconazole, myclobutanil, penconazole, propiconazole, prothioconazole, simeconazole, tebuconazole, tetraconazole, triadimenol, triadimefon, triticonazole;
  imidazoles: cyazofamid, imazalil, pefurazoate, triflumizole;
  benzimidazoles: benomyl, carbendazim, fuberidazole, thiabendazole;
  others: ethaboxam, etridiazole, hymexazole;
strobilurins
  azoxystrobin, dimoxystrobin, enestroburin, fluoxastrobin, kresoxim-methyl, metominostrobin, picoxystrobin, pyraclostrobin, trifloxystrobin, orysastrobin, methyl (2-chloro-5-[1-(3-methylbenzyloxyimino)ethyl]benzyl)carbamate, methyl (2-chloro-5-[1-(6-methylpyridin-2-ylmethoxyimino)ethyl]benzyl)carbamate, methyl 2-(ortho-(2,5-dimethylphenyloxymethylene)phenyl)-3-methoxyacrylate;
carboxamides
  carboxanilides: benalaxyl, benodanil, boscalid, carboxin, mepronil, fenfuram, fenhexamid, flutolanil, furametpyr, metalaxyl, ofurace, oxadixyl, oxycarboxin, penthiopyrad, thifluzamide, tiadinil, N-(4'-bromobiphenyl-2-yl)-4-difluoromethyl-2-methylthiazole-5-carboxamide, N-(4'-trifluoromethylbiphenyl-2-yl)-4-difluoro-methyl-2-methylthiazole-5-carboxamide, N-(4'-chloro-3'- fluorobiphenyl-2-yl)-4-difluoromethyl-2-methylthiazole-5-carboxamide, N-(3',4'-dichloro-4-fluorobiphenyl-2-yl)-3-difluoromethyl-1-methylpyrazole-4-carboxamide, N-(2-cyanophenyl)-3,4-dichloroisothiazole-5-carboxamide;

carboxylic acid morpholides: dimethomorph, flumorph;

benzamides: flumetover, fluopicolide (picobenzamid), zoxamide;

other carboxamides: carpropamid, diclocymet, mandipropamid, N-(2-(4-[3-(4-chlorophenyl)prop-2-ynyloxy]-3-methoxyphenyl)ethyl)-2-methanesulfonylamino-3-methylbutyramide, N-(2-(4-[3-(4-chlorophenyl)prop-2-ynyloxy]-3-methoxyphenyl)ethyl)-2-ethanesulfonylamino-3-methylbutyramide;

nitrogenous heterocyclyl compounds pyridines: pyrifenox, 3-[5-(4-chlorophenyl)-2,3-dimethyl-isoxazolidin-3-yl]pyridine;

pyrimidines: bupirimate, ferimzone, fenarimol, mepanipyrim, nuarimol, pyrimethanil;

piperazines: triforine;

pyrroles: fludioxonil, fenpiclonil;

morpholines: aldimorph, dodemorph, fenpropimorph, tridemorph;

dicarboximides: iprodione, procymidone, vinclozolin;

others: acibenzolar-5-methyl, anilazine, captan, captafol, dazomet, diclomezine, fenoxanil, folpet, fenpropidin, famoxadone, fenamidone, octhilinone, probenazole, proquinazid, pyroquilon, quinoxyfen, tricyclazole, 5-chloro-7-(4-methylpiperidin-1-yl)-6-(2,4,6-trifluorophenyl)-[1,2,4]triazolo[1,5-a]pyrimidine, 2-butoxy-6-iodo-3-propyl-chromen-4-one, N,N-dimethyl-3-(3-bromo-6-fluoro-2-methylindole-1-sulfonyl)-[1,2,4]triazole-1-sulfonamide;

carbamates and dithiocarbamates dithiocarbamates: ferbam, mancozeb, maneb, metiram, metam, propineb, thiram, zineb, ziram;

carbamates: diethofencarb, flubenthiavalicarb, iprovalicarb, propamocarb, methyl 3-(4-chlorophenyl)-3-(2-isopropoxycarbonylamino-3-methylbutyrylamino)propionate, 4-fluorophenyl N-(1-(1-(4-cyanophenyl)ethanesulfonyl)but-2-yl)carbamate;

other fungicides guanidines: dodine, iminoctadine, guazatine;

antibiotics: kasugamycin, polyoxins, streptomycin, validamycin A;

organometallic compounds: fentin salts;

sulfur-containing heterocyclyl compounds: isoprothiolane, dithianon;

organophosphorus compounds: edifenphos, fosetyl, fosetyl-aluminum, iprobenfos, pyrazophos, tolclofos-methyl, phosphorous acid and its salts;

organochlorine compounds: thiophanate-methyl, chlorothalonil, dichlofluanid, tolyl-fluanid, flusulfamide, phthalide, hexachlorobenzene, pencycuron, quintozene;

nitrophenyl derivatives: binapacryl, dinocap, dinobuton;

inorganic active compounds: Bordeaux mixture, copper acetate, copper hydroxide, copper oxychloride, basic copper sulfate, sulfur;

others: spiroxamine, cyflufenamid, cymoxanil, metrafenone.

The active compounds can also be used in the form of their agriculturally acceptable salts. Suitable for this purpose are, in general, alkali or alkaline earth metal salts, such as sodium, potassium or calcium salts.

Compound I and compound II are usually applied in a weight ratio of from 100:1 to 1:100, preferably from 20:1 to 1:20, in particular from 10:1 to 1:10.

The other active components are, if desired, added in a ratio of from 20:1 to 1:20 to the compound I.

Depending on the type of compound and the effect desired, the application rates of the mixtures according to the invention are from 5 g/ha to 2000 g/ha, preferably from 50 to 900 g/ha, in particular from 50 to 750 g/ha.

Correspondingly, the application rates for the compound I are generally from 1 to 1000 g/ha, preferably from 10 to 900 g/ha, in particular from 20 to 750 g/ha.

Correspondingly, the application rates for the active compound II are generally from 1 to 2000 g/ha, preferably from 10 to 900 g/ha, in particular from 40 to 500 g/ha.

The application rates of the mixture used in the treatment of seed, for example by dusting, coating or drenching seed, are usually from 1 to 1000 g/100 kg of seed, preferably from 1 to 750 g/100 kg, in particular from 5 to 500 g/100 kg.

When used in the protection of materials or stored products, the amount of active compound applied depends on the kind of application area and on the desired effect.

Amounts customarily applied in the protection of materials are, for example, 0.001 g to 2 kg, preferably 0.005 g to 1 kg, of active compound per cubic meter of treated material.

The method for controlling harmful fungi is carried out by separate or joint application of the compound I and the compound II or the mixtures of the compound I and the compound II by spraying or dusting the seeds, the plants or the soils before or after sowing of the plants or before or after emergence of the plants.

The mixtures according to the invention, or the compound I and the compound II, can be converted to the customary formulations, for example solutions, emulsions, suspensions, dusts, powders, pastes and granules. The use form depends on the particular intended use; it should in each case ensure a fine and uniform distribution of the compound according to the invention.

The formulations are prepared in a known manner, for example by extending the active compound with solvents and/or carriers, if desired using emulsifiers and dispersants. Solvents/auxiliaries which are suitable for this purpose are essentially:

water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used, carriers such as ground natural minerals (for example kaolins, clays, talc, chalk) and ground synthetic minerals (for example finely divided silica, silicates); emulsifiers such as nonionic and anionic emulsifiers (for example polyoxyethylene fatty alcohol ethers, alkylsulfonates and arylsulfonates) and dispersants such as lignosulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenol polyglycol ethers, tributylphenyl polyglycol ether, tristerylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for broadcasting and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nut-shell meal, cellulose powders and other solid carriers.

In general, the formulations comprise from 0.01 to 95% by weight, preferably from 0.1 to 90% by weight, of the active compound. The active compounds are employed in a purity of from 90% to 100%, preferably 95% to 100% (according to NMR spectrum).

The following are examples of formulations: 1. products for dilution with water

A Water-Soluble Concentrates (SL, LS)

10 parts by weight of the active compounds are dissolved in 90 parts by weight of water or a water-soluble solvent. As an alternative, wetting agents or other auxiliaries are added. The active compound dissolves upon dilution with water. In this way, a formulation having a content of 10% by weight of active compound is obtained.

B Dispersible Concentrates (DC)

20 parts by weight of the active compounds are dissolved in 70 parts by weight of cyclohexanone with addition of 10 parts by weight of a dispersant, for example polyvinylpyrrolidone. Dilution with water gives a dispersion. The active compound content is 20% by weight.

C Emulsifiable Concentrates (EC)

15 parts by weight of the active compounds are dissolved in 75 parts by weight of xylene with addition of calcium dodecylbenzenesulfonate and castor oil ethoxylate (in each case 5 parts by weight). Dilution with water gives an emulsion. The formulation has an active compound content of 15% by weight.

D Emulsions (EW, EO, ES)

25 parts by weight of the active compounds are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (e.g. Ultraturrax) and made into a homogeneous emulsion. Dilution with water gives an emulsion. The formulation has an active compound content of 25% by weight.

E Suspensions (SC, OD, FS)

In an agitated ball mill, 20 parts by weight of the active compounds are comminuted with addition of 10 parts by weight of dispersants and wetting agents and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules (WG, SG)

50 parts by weight of the active compounds are ground finely with addition of 50 parts by weight of dispersants and wetting agents and prepared as water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders (WP, SP, SS, WS)

75 parts by weight of the active compounds are ground in a rotor-stator mill with addition of 25 parts by weight of dispersants, wetting agents and silica gel. Dilution with water gives a stable dispersion or solution of the active compound. The active compound content of the formulation is 75% by weight.

H Gel Formulations (GF)

In a ball mill, 20 parts by weight of the active compounds, 10 parts by weight of dispersant, 1 part by weight of gelling agent and 70 parts by weight of water or an organic solvent are ground to give a fine suspension. On dilution with water, a stable suspension having an active compound content of 20% by weight is obtained.

2. Products to be applied undiluted

I Dustable Powders (DP, DS)

5 parts by weight of the active compounds are ground finely and mixed intimately with 95 parts by weight of finely divided kaolin. This gives a dustable product having an active compound content of 5% by weight.

J Granules (GR, FG, GG, MG)

0.5 part by weight of the active compounds is ground finely and associated with 99.5 parts by weight of carriers. Current methods are extrusion, spray-drying and the fluidized bed. This gives granules to be applied undiluted having an active compound content of 0.5% by weight.

K ULV Solutions (UL)

10 parts by weight of the active compounds are dissolved in 90 parts by weight of an organic solvent, for example xylene. This gives a product to be applied undiluted having an active compound content of 10% by weight.

For seed treatment, use is usually made of water-soluble concentrates (LS), suspensions (FS), dustable powders (DS), water-dispersible and water-soluble powders (WS, SS), emulsions (ES), emulsifiable concentrates (EC) and gel formulations (GF). These formulations can be applied to the seed in undiluted form or, preferably, diluted. Application can be carried out prior to sowing.

The active compounds can be used as such, in the form of their formulations or of the use forms prepared therefrom, e.g. in the form of directly sprayable solutions, powders, suspensions or dispersions, emulsions, oil dispersions, pastes, dustable products, materials for broadcasting or granules, by means of spraying, atomizing, dusting, broadcasting or watering. The use forms depend entirely on the intended purposes; they should always ensure the finest possible distribution of the active compounds according to the invention.

Aqueous use forms can be prepared from emulsifiable concentrates, pastes or wettable powders (spray powders, oil dispersions) by addition of water. To prepare emulsions, pastes or oil dispersions, the substances can be homogenized in water, as such or dissolved in an oil or solvent, by means of wetting agents, tackifiers, dispersants or emulsifiers. However, it is also possible to prepare concentrates comprising active substance, wetting agent, tackifier, dispersant or emulsifier and possibly solvent or oil which are suitable for dilution with water.

The concentrations of active compound in the ready-for-use preparations can be varied within relatively wide ranges. In general, they are between 0.0001 and 10%, preferably between 0.01 and 1%.

The active compounds can also be used with great success in the ultra-low volume (ULV) process, it being possible to apply formulations with more than 95% by weight of active compound or even the active compound without additives.

Oils of various types, wetting agents, adjuvants, herbicides, fungicides, other pesticides and bactericides can be added to the active compounds, if appropriate also not until immediately before use (tank mix). These agents can be added to the compositions according to the invention in a weight ratio of 1:100 to 100:1, preferably of 1:10 to 10:1.

USE EXAMPLES

The fungicidal action of the compounds and the mixtures can be demonstrated by the following tests:

Active Compound Preparation

The active compounds were prepared jointly or separately as a stock solution comprising 25 mg of active compound which was made up to 10 ml using a mixture of acetone and/or DMSO and the emulsifier Wettol EM 31 (wetting agent having emulsifying and dispersing action based on ethoxylated alkylphenols) in a volume ratio of solvent/emulsifier of 99 to 1. The mixture was then made up with water to 100 ml. This stock solution was diluted with the solvent/emulsifier/water mixture described to the concentration of active compounds stated below.

Use Example 1

Activity Against Gray Mold on Bell Pepper Leaves Caused by *Botrytis cinerea*, 1 Day Protective Application Bell pepper seedlings were, after 2-3 leaves were well-developed, sprayed to runoff point with an aqueous suspension having the active compound concentration stated below. The next day, the treated plants were inoculated with a spore suspension of *Botrytis cinerea* in a 2% strength biomalt solution. The test plants were then placed in a dark climatized chamber at 22 to 24° C. and high atmospheric humidity. After 5 days, the extent of the fungal infection on the leaves could be determined visually in %.

TABLE 1

| Active compound/active compound combination | Conc. (ppm) | Ratio | Observed effect (%) | Effect calculated using Colby's formula (%) | Synergism | Level of synergism (%) |
|---|---|---|---|---|---|---|
| Metconazole | 0.016 | | 0 | | | |
| Prochloraz | 0.25 | | 0 | | | |
| Metconazole | 0.016 | 1:16 | 50 | 0 | Yes | 50 |
| Prochloraz | 0.25 | | | | | |

Use Example 2

Protective Activity Against *Puccinia recondita* on Wheat (Brown Rust of Wheat)

Leaves of potted wheat seedlings were sprayed to runoff point with an aqueous suspension having the active compound concentration stated below. The next day, the treated plants were inoculated with a spore suspension of brown rust of wheat (*Puccinia recondita*). The plants were then placed in a chamber with high atmospheric humidity (90 to 95%) at 20 to 22° C. for 24 hours. During this time, the spores germinated and the germ tubes penetrated into the leaf tissue. The following day, the test plants were returned to the greenhouse and cultivated at temperatures between 20 and 22° C. and at 65 to 70% relative atmospheric humidity for a further 7 days. The extent of the rust fungus development on the leaves was then determined visually.

TABLE 2

| Active compound/active compound combination | Conc. (ppm) | Ratio | Observed effect (%) | Effect calculated using Colby's formula (%) | Synergism | Level of synergism (%) |
|---|---|---|---|---|---|---|
| Metconazole | 0.25 | | 13 | | | |
| Prochloraz | 4 | | 0 | | | |
| Metconazole | 0.25 | 1:16 | 38 | 13 | Yes | 25 |
| Prochloraz | 4 | | | | | |

The visually determined percentages of infected leaf areas were converted into efficacies as % of the untreated control:

The efficacy (E) is calculated as follows using Abbot's formula:

$$E = (1 - \alpha/\beta) \cdot 100$$

α corresponds to the fungicidal infection of the treated plants in % and

β corresponds to the fungicidal infection of the untreated (control) plants in %

An efficacy of 0 means that the infection level of the treated plants corresponds to that of the untreated control plants; an efficacy of 100 means that the treated plants are not infected.

The expected efficacies of combinations of active compounds were determined using Colby's formula (Colby, S. R. "Calculating synergistic and antagonistic responses of herbicide Combinations", Weeds, 15, 20-22, 1967) and compared with the observed efficacies.

Colby's formula:

$$E = x + y - x \cdot y/100$$

E expected efficacy, expressed in % of the untreated control, when using the mixture of the active compounds A and B at the concentrations a and b x efficacy, expressed in % of the untreated control, when using the active compound A at the concentration a y efficacy, expressed in % of the untreated control, when using the active compound B at the concentration b The results of the tests in Tables 1 and 2 show that, by virtue of the synergism, the activity of the mixtures according to the invention is considerably higher than had been predicted using Colby's formula.

The invention claimed is:

1. A fungicidal mixture comprising, as active components:
1) metconazole of the formula I

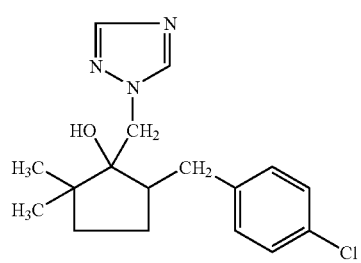

and
2) prochloraz of the formula II,

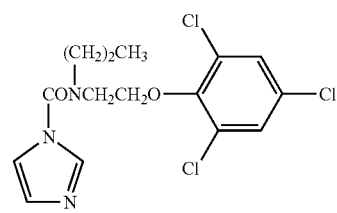

in a synergistically effective amount.

2. The fungicidal mixture of claim 1, comprising the compound of the formula I and the compound of the formula II in a weight ratio of from 100:1 to 1:100.

3. The fungicidal mixture of claim 1, comprising a further active compound.

4. A fungicidal composition, comprising a liquid or solid carrier and a mixture of claim 1.

5. Seed, comprising a mixture of claim 1 in an amount of from 1 to 1000 g/100 kg of seeds.

6. A method for controlling phytopathogenic harmful fungi, which comprises treating the fungi, their habitat or the plants to be protected against fungal attack, the soil or seeds with a mixture of claim 1.

7. The method of claim 6, wherein said mixture is applied in an amount of from 5 g/ha to 2000 g/ha.

8. The method of claim 6, wherein said mixture is applied in an amount of from 1 to 1000 g/100 kg of seed.

9. A method for controlling phytopathogenic harmful fungi, which comprises treating the fungi, their habitat or the plants to be protected against fungal attack, the soil or seeds with a synergistically effective amount of the compound I

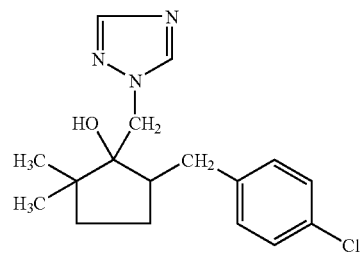

and the compound II

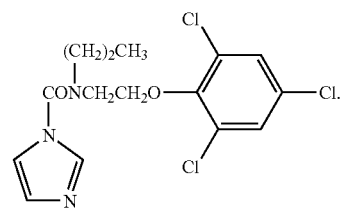

10. The method of claim 9, wherein said compounds I and II are applied simultaneously, that is jointly or separately, or in succession.

11. The method of claim 9, wherein said compounds I and II are applied in an amount of from 5 g/ha to 2000 g/ha.

12. The method of claim 9, wherein said compounds I and II are applied in an amount of from 1 to 1000 g/100 kg of seed.

13. The method of claim 9, wherein *Phakopsora* species are controlled.

\* \* \* \* \*